(12) United States Patent
Hosokawa et al.

(10) Patent No.: US 10,788,502 B2
(45) Date of Patent: Sep. 29, 2020

(54) ERYTHROCYTE SEDIMENTATION INHIBITOR

(71) Applicant: FUJIMORI KOGYO CO., LTD., Tokyo (JP)

(72) Inventors: Kazuya Hosokawa, Tokyo (JP); Tomoko Wada, Tokyo (JP)

(73) Assignee: FUJIMORI KOGYO CO., LTD., Tokyo (JP)

( * ) Notice: Subject to any disclaimer, the term of this patent is extended or adjusted under 35 U.S.C. 154(b) by 0 days.

(21) Appl. No.: 15/116,305

(22) PCT Filed: Feb. 3, 2015

(86) PCT No.: PCT/JP2015/052988
§ 371 (c)(1),
(2) Date: Aug. 3, 2016

(87) PCT Pub. No.: WO2015/119115
PCT Pub. Date: Aug. 13, 2015

(65) Prior Publication Data
US 2017/0010289 A1 Jan. 12, 2017

(30) Foreign Application Priority Data
Feb. 6, 2014 (JP) .................................. 2014-021359

(51) Int. Cl.
*G01N 33/86* (2006.01)
*G01N 33/80* (2006.01)
*G01N 33/49* (2006.01)

(52) U.S. Cl.
CPC ........... *G01N 33/86* (2013.01); *G01N 33/491* (2013.01); *G01N 33/80* (2013.01)

(58) Field of Classification Search
None
See application file for complete search history.

(56) References Cited

U.S. PATENT DOCUMENTS

| 6,004,819 | A | * | 12/1999 | Gorog | ................ | G01N 33/4905 |
|---|---|---|---|---|---|---|
| | | | | | | 422/73 |
| 2002/0084221 | A1 | | 7/2002 | Verkaart et al. | | |
| 2008/0248012 | A1 | | 10/2008 | Suematsu | | |
| 2009/0311675 | A1 | | 12/2009 | Hosokawa | | |
| 2011/0151500 | A1 | | 6/2011 | Hosokawa et al. | | |
| 2013/0164176 | A1 | | 6/2013 | Hosokawa | | |
| 2013/0164855 | A1 | | 6/2013 | Hosokawa | | |

FOREIGN PATENT DOCUMENTS

| JP | 2004-529076 | 9/2004 |
|---|---|---|
| WO | WO-2005/072773 | 8/2005 |
| WO | WO-2007/046450 | 4/2007 |
| WO | WO-2010/018833 | 2/2010 |

OTHER PUBLICATIONS

Falke et al. "Molecular mechanisms of band 3 inhibitors. 1. Transport site inhibitors." Biochemistry 25.24 (1986): 7888-7894. (Year: 1986).*
International Search Report for PCT/JP2015/052988 dated Apr. 28, 2015.
Written Opinion ofthe International Searching Authority for PCT/JP2015/052988 dated Apr. 28, 2015.
International Preliminary Report on Patentability for PCT/JP2015/052988 dated Aug. 9, 2016.
International Preliminary Report on Patentability for PCT/JP2015/052988 dated Aug. 18, 2016.
James M. Salhany, Cell, Mol. Biol., 1996, 42(7), 1065-1096.
Joseph J. Falke et al., Biochemistry, 1986, 25(24), 7895-7898.
Ingolf Bernhardt, et al., "Application of digital holographic microscopy to investigate the sedimentation of intact red blood cells and their interaction with artificial surfaces", Bioelectrochemistry, vol. 73, No. 2, 2008, pp. 92-96.
Jespser Brahm, "The permeability of red blood cells to chloride, urea and water", Journal of Experimental Biology, vol. 216, 2013, pp. 2238-2246.
Kazuaki Yokoyama, et al., "A possible role for extracellular bicarbonate in U-46619-induced rat platelet aggregation", Thrombosis Research, vol. 74, No. 4, 1994, pp. 369-376.
Kiaran Kirk, et al., "Glibenclamide and meglitinide block the transport of low molecular weight solutes into malaria-infected erythrocytes", FEBS Letters, vol. 323, Nos. 1-2, 1993, pp. 123-128.
Robert J. Smith, et al., "Effects of an Anion Channel Blocker, 4,4'-Diisothiocyano-2,2'-Disulfonic Acid Stilbene (DIDS), on Human Neutrophil Function", Biochemical and Biophysical Research Communications, vol. 120, No. 3, 1984, pp. 964-972.
S.S. Norris, et al., "Evaluation of 4,4'-diisothiocyanatostilbene-2,2'-disulfonic acid in the inhibition of rouleaux formation", Transfusion, vol. 36, 1996, pp. 109-112.
Shuji Kitagawa, et al., "Inhibitory effects of 4,4'-diisothiocyanostilbene-2,2'-disulfonate (DIDS) on the ADP-stimulated aggregation of gel-filtered bovine blood platelets", Biochemical and Biophysical Research Communications, vol. 111, No. 1, 1983, pp. 306-311.
Song-Mei Yin, et al., "The effects of chloride channel blockers on thrombocytic cytoplasmic free calcium concentration and platelet aggregation", Chinese Journal of Hematology, vol. 26, No. 3, 2005, pp. 170-174.
Yukio Ozaki, et al., "Effects of five anion channel blockers on thrombin- and ionomycin-activated platelet functions", Biochemical Pharmacology, vol. 38, No. 13, 1989, pp. 2147-2152.

(Continued)

*Primary Examiner* — Emily A Cordas
(74) *Attorney, Agent, or Firm* — Foley & Lardner LLP

(57) ABSTRACT

The present invention addresses a problem in which, when examining blood properties in measurements of thrombus formation capacity and platelet function or the like, measurement data is changed as a result of sedimentation of blood in reservoirs during measurement. An erythrocyte membrane ion transport inhibitor, such as disodium 4,4'-dinitrostilbene-2,2'-disulfonate (DNDS) or 4,4'-diisothiocyanatostilbene-2,2'-disulfonic acid (DIDS), is used to inhibit erythrocyte sedimentation, and accurate measurement data is obtained.

3 Claims, 3 Drawing Sheets

(56) References Cited

OTHER PUBLICATIONS

Extended European Search Report issued in European Patent Application No. 15746241.7 dated Oct. 4, 2017.
Sing-Mei Yin, et al., "The effects of chloride channel blockers on thrombocytic cytoplasmic free calcium concentration and platelet aggregation", Chinese Journal of Hematology, vol. 26, No. 3, 2005, pp. 170-174.

* cited by examiner

ERYTHROCYTE SEDIMENTATION INHIBITOR

TECHNICAL FIELD

The present invention relates to an erythrocyte sedimentation inhibitor which is useful for tests for blood properties, such as measurement of the thrombogenic capacity and the platelet function.

BACKGROUND ART

Erythrocyte sedimentation (blood sedimentation) is a phenomenon that occurs, for example, due to weakening of repulsion between erythrocytes caused by an increase in basic proteins, γ-globulin, or α2-macroglobulin, or by a decrease in acidic proteins (mainly albumin), or due to a decrease in erythrocytes caused by anemia. Measurement of the erythrocyte sedimentation rate is used for tests for diseases.

In the measurement of the erythrocyte sedimentation rate, a blood sedimentation tube containing blood is left to stand vertically, and the amount of sedimentation of erythrocytes is measured for a predetermined period (30 minutes to 2 hours) (normal value for Japanese, 1 to 15 mm/hour). It is known that, even in a healthy blood sample, sedimentation of erythrocytes is promoted by inclining of the blood container since this causes rolling of erythrocytes on the wall or bottom of the container.

Methods for measuring the thrombogenic capacity, platelet function, and the like using collected blood are known (Patent Documents 1 and 2). In these methods, in cases where the collected blood undergoes separation of erythrocytes from the plasma component due to erythrocyte sedimentation before being subjected to a test requiring a long time (about 10 to 30 minutes), accurate measurement results cannot be obtained because of an increase in the hematocrit of the blood sample at the bottom of the container, which is problematic.

4,4'-Diisothiocyanatostilbene-2,2'-disulfonic acid (DIDS) and disodium 4,4'-dinitrostilbene-2,2'-disulfonate (DNDS) are ion transport inhibitors that immobilize band 3 by covalent bonding from the outside of the membrane (Non-patent Documents 1 and 2). Their association with erythrocyte sedimentation is not known.

PRIOR ART DOCUMENTS

Patent Documents

Patent Document 1: WO 2007/046450
Patent Document 2: WO 2010/018833

Non-Patent Documents

Non-patent Document 1: Cell Mol Biol (Noisy-le-grand). 1996 November; 42(7): 1065-96.
Non-patent Document 2: Biochemistry. 1986 Dec. 2; 25(24): 7895-8.

SUMMARY OF THE INVENTION

Problems to be Solved by the Invention

In tests for blood properties such as measurement of the thrombogenic capacity and the platelet function in which the measurement is carried out while blood is left to stand for a predetermined period (10 to 30 minutes), sedimentation of erythrocytes in the blood sample in the reservoir may occur during the measurement, causing separation of the plasma component from the blood cell component, which affects the measurement data. In order to solve this problem, the present invention aims to provide means for suppressing the erythrocyte sedimentation (blood sedimentation) for obtaining accurate measurement data.

Means for Solving the Problems

In order to solve the problem described above, the present inventors intensively studied and found that ion transport inhibitors such as DIDS and DNDS inhibit erythrocyte sedimentation without affecting the thrombogenic capacity and the platelet function, and that, by processing blood using such ion transport inhibitors, accurate data can be obtained in tests for blood properties such as measurement of the thrombogenic capacity and the platelet function, thereby completed the present invention.

That is, the present invention provides the following.
(1) An erythrocyte sedimentation inhibitor comprising an ion transport inhibitor for erythrocyte membrane.
(2) The erythrocyte sedimentation inhibitor according to (1), wherein the ion transport inhibitor is a band 3 immobilizer.
(3) The erythrocyte sedimentation inhibitor according to (2), wherein the band 3 immobilizer is 4,4'-diisothiocyanatostilbene-2,2'-disulfonic acid (DIDS) or disodium 4,4'-dinitrostilbene-2,2'-disulfonate (DNDS).
(4) The erythrocyte sedimentation inhibitor according to (3), wherein DIDS is added to blood to a final concentration of not less than 0.15 mg/ml.
(5) The erythrocyte sedimentation inhibitor according to (3), wherein DNDS is added to blood to a final concentration of not less than 0.02 mg/ml.
(6) A method for testing a blood property, comprising testing the blood property using blood treated with the erythrocyte sedimentation inhibitor according to any one of (1) to (5).
(7) The method for testing a blood property according to (6), wherein thrombogenic capacity and/or platelet function are/is measured.

Effect of the Invention

According to the present invention, by treating blood with an ion transport inhibitor such as DIDS or DNDS, influence of blood sedimentation can be eliminated in tests for blood properties such as measurement of the thrombogenic capacity and the platelet function. Therefore, accurate measurement data can be obtained.

EMBODIMENTS FOR CARRYING OUT THE INVENTION

Figure 1:
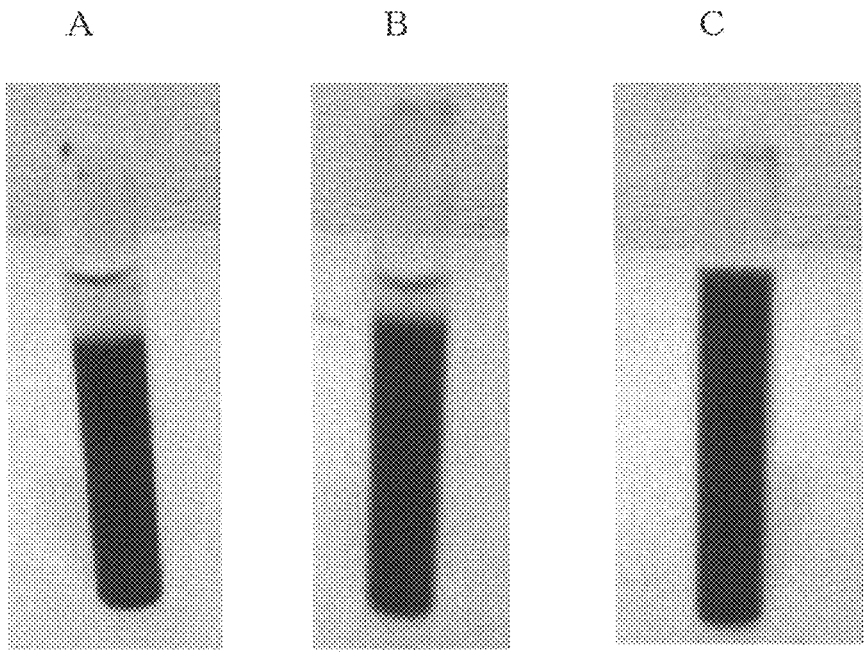
FIG. 1 shows photographs showing blood sedimentation in glass tubes (A, without addition of DIDS; B, addition of 0.15 mg/ml DIDS; C, addition of 1.5 mg/ml DIDS).

The erythrocyte sedimentation inhibitor of the present invention comprises an ion (e.g., chloride ion) transport inhibitor for erythrocyte membrane. Examples of the ion transport inhibitor for erythrocyte membrane include band 3 immobilizers.

Here, band 3 (also referred to as AE1) is a membrane transport protein present in the cell membrane of erythrocytes (erythrocyte membrane) in a large amount. It is known that band 3 detects carbon dioxide dissolved in blood, and promotes release of oxygen from hemoglobin present in erythrocytes (Leg Med (Tokyo). 2005 July; 7(4): 270-3. Molecular aspects of Rh antigens). This function is based on the ion exchange transport mechanism, and allows preferential release of oxygen in metabolically active tissues, thereby enabling distribution of oxygen in appropriate amounts.

The band 3 immobilizer is not limited as long as it binds to band 3 to inhibit ion transport by band 3. The band 3 immobilizer is preferably DIDS or DNDS.

It is thought that addition of an ion transport inhibitor for erythrocyte membrane such as DIDS to blood causes immobilization of band 3 of erythrocytes, which leads to an increase in the membrane potential to cause repulsion between the erythrocytes, resulting in suppression of the sedimentation.

DIDS is preferably added to the blood to a final concentration of not less than 0.15 mg/ml, more preferably added to the blood to a final concentration of not less than 0.50 mg/ml, still more preferably added to the blood to a final concentration of not less than 1.00 mg/ml.

DNDS is preferably added to the blood to a final concentration of not less than 0.02 mg/ml, more preferably added to the blood to a final concentration of not less than 0.10 mg/ml, still more preferably added to the blood to a final concentration of not less than 0.20 mg/ml.

The upper limit of the concentration is not limited as long as tests using the blood are not inhibited. The concentration is, for example, not more than 100.00 mg/ml.

The ion transport inhibitor for erythrocyte membrane such as DIDS or DNDS is preferably added to the blood after being suspended or dissolved in water, physiological saline, or the like.

The blood is preferably anticoagulated whole blood.

Since DNDS is soluble in water, an aqueous DNDS solution is suitable as a reagent to be added to the blood. For example, a mixed aqueous solution of DNDS and one or more of anticoagulants such as citric acid, hirudin, and trypsin inhibitors, and reagents such as calcium, may be prepared.

The ion transport inhibitor for erythrocyte membrane such as DIDS may be added to the blood either immediately after the blood collection, or immediately before the measurement.

In blood subjected to the erythrocyte sedimentation-inhibiting treatment using the ion transport inhibitor for erythrocyte membrane such as DIDS or DNDS, sedimentation of erythrocytes is suppressed while the thrombogenic capacity and the platelet function are not affected. Therefore, such blood can be subjected to tests for blood properties such as measurement of the thrombogenic capacity and the platelet function. In particular, in cases of a test including the process of leaving blood to stand for a predetermined period (about 10 minutes to 1 hour), sedimentation of erythrocytes in the blood sample is effectively suppressed.

For example, as described in the above Patent Documents 1 and 2, blood may be allowed to flow in a channel formed in a microchip, and thrombus formation in the channel may be analyzed. In the methods described in these documents, a microchip channel to which collagen, a mixture of collagen and tissue factors, or the like is applied is perfused for a predetermined period (10 to 30 minutes) with a blood sample fed from a blood container to analyze formation of platelet thrombi or thrombi composed of fibrin and platelets in the channel. By this, the blood sample can be analyzed for its thrombogenic capacity, platelet activation capacity, and the like. However, in cases where sedimentation of erythrocytes in the blood sample occurs in the blood container that is left to stand during the measurement period, resulting in separation of the erythrocytes from the plasma component, properties such as hematocrit largely vary between the upper layer and the lower layer of the blood sample. In such measurement, a more accurate test for blood properties is possible by adding DIDS or DNDS to suppress erythrocyte sedimentation in the blood sample contained in the blood container, without affecting the thrombogenic capacity and the platelet function. However, test methods using blood processed with the erythrocyte sedimentation inhibitor of the present invention are not limited to these embodiments.

EXAMPLES

The present invention is described below more concretely by way of Examples. However, the present invention is not limited to the following embodiments.

Example 1

Figure 2:
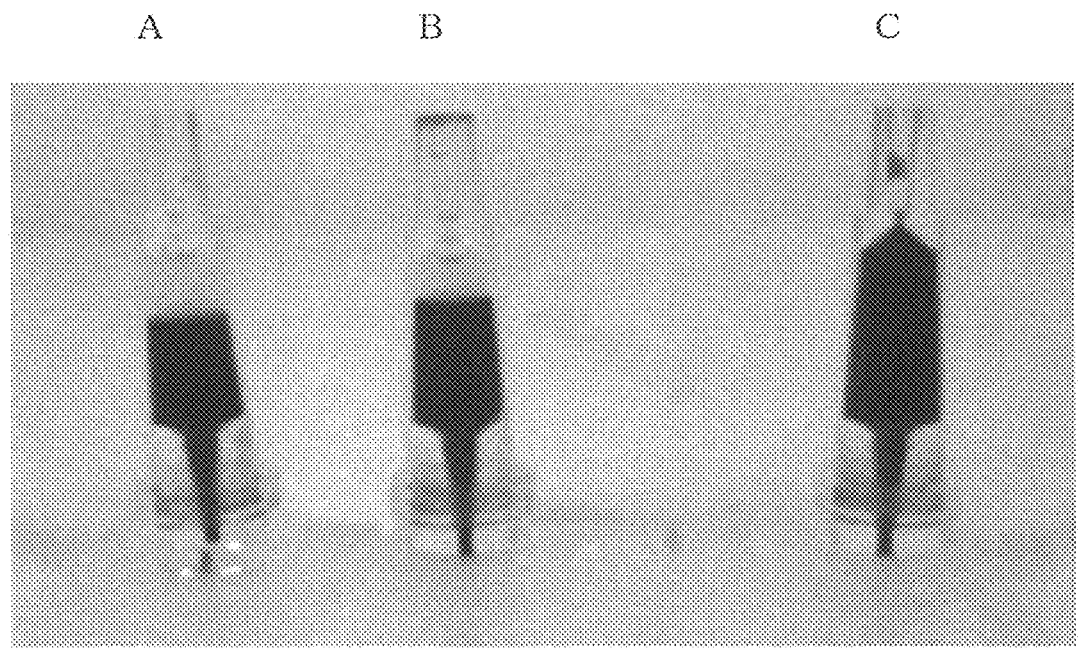
FIG. 2 shows photographs showing blood sedimentation in blood containers for measurement of thrombus formation (A, without addition of DIDS; B, addition of 0.15 mg/ml DIDS; C, addition of 1.5 mg/ml DIDS).

A solution of DIDS (Tokyo Chemical Industry Co., Ltd.) in physiological saline was added to blood anticoagulated with sodium citrate to a final concentration of 0.15 mg/ml or 1.5 mg/ml, respectively. The resulting mixture was mixed, and placed in a glass tube having a diameter of 6 mm (FIG. 1) or a blood container for measurement of thrombus formation (FIG. 2), followed by being left to stand.

As a result, 30 minutes later, blood sedimentation was found to be rather suppressed in the cases of the 0.15 mg/ml solution. In the cases of the 1.5 mg/ml solution, blood sedimentation was completely suppressed even in a glass tube and a container having an inclined bottom (blood container for measurement of thrombus formation).

Figure 3:
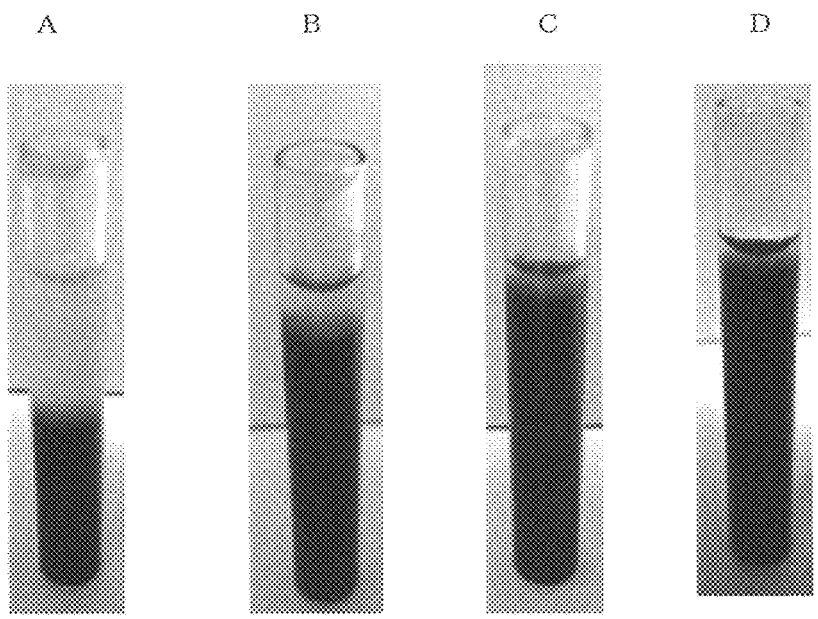
FIG. 3 shows photographs showing blood sedimentation in glass tubes (A, without addition of DNDS; B, addition of 0.02 mg/ml DNDS; C, addition of 0.1 mg/ml DNDS; D, addition of 0.2 mg/ml DNDS).

A solution of DNDS (Tokyo Chemical Industry Co., Ltd.) in physiological saline was added to blood anticoagulated with sodium citrate to a final concentration of 0.02 mg/ml, 0.1 mg/ml, or 0.2 mg/ml, respectively. The resulting mixture was mixed, and placed in a glass tube having a diameter of 6 mm (FIG. 3), followed by being left to stand.

As a result, 30 minutes later, blood sedimentation was found to be suppressed in the cases of the 0.02 mg/ml and 0.1 mg/ml solutions relative to the control. In the case of the 0.2 mg/ml solution, blood sedimentation was almost completely suppressed.

Figure 4:
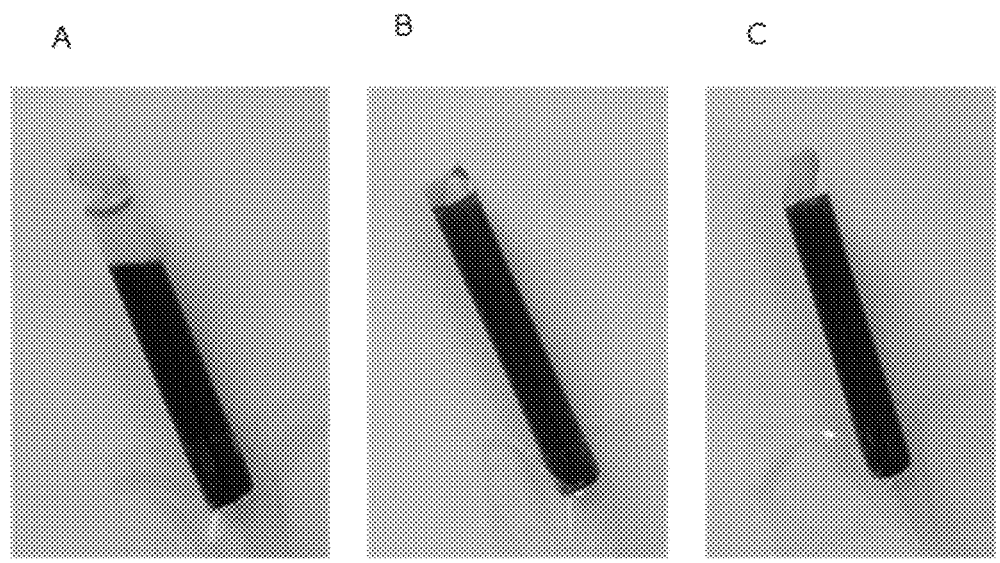
FIG. 4 shows photographs showing blood sedimentation in glass tubes (A, without addition of DNDS; B, addition of 0.5 mg/ml DNDS; C, addition of 1 mg/ml DNDS).

A solution of DNDS (Tokyo Chemical Industry Co., Ltd.) in physiological saline was added to blood anticoagulated with sodium citrate to a final concentration of 0.5 mg/ml or 1.0 mg/ml, respectively. The resulting mixture was mixed, and placed in a glass tube having a diameter of 6 mm. The glass tube was then inclined at an angle of 30°, and left to stand (FIG. 4).

As a result, 30 minutes later, blood sedimentation was found to be suppressed in the cases of the 0.5 mg/ml and 1.0 mg/ml solutions relative to the control.

Example 2

The apparatus described in FIG. 12 of Patent Document 1 was used.

A capillary having a width of 300 µm, depth of 80 µm, and length of 1.5 cm formed on a microchip was coated with type I collagen (manufactured by Nitta Gelatin Inc.) and tissue thromboplastin (manufactured by Sysmex Corporation). The capillary was perfused with citrate blood supplemented with CTI (corn trypsin inhibitor) (final concentration, 50 µg/ml), calcium chloride (final concentration, 12 mM), and DIDS (final concentration, 0 or 1.5 mg/ml) or DNDS (final concentration, 0.3 mg/ml) fed from a blood container at a flow rate of 10 µl/min for 30 minutes, while changes in the pressure caused by formation of thrombi composed of fibrin and platelets were continuously measured.

Figure 5:
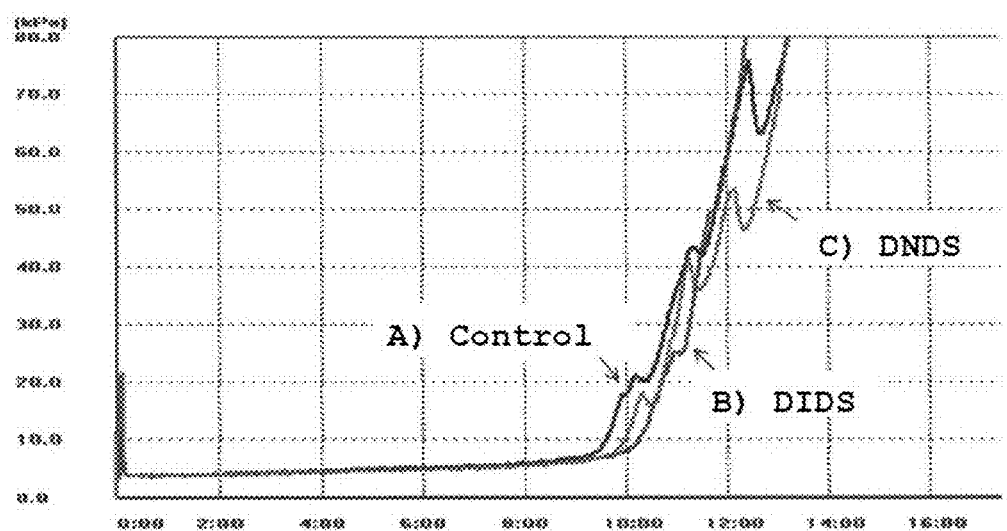
FIG. 5 is a graph showing pressure patterns during perfusion with blood samples. A, without addition of DIDS; B, addition of DIDS (1.5 mg/ml); C, addition of DNDS (0.3 mg/ml).

FIG. 5 is a graph showing the pressure patterns during the perfusion with blood samples. The pressure reflects formation of thrombi composed of fibrin and activated platelets, and comprehensively reflects the blood coagulation capacity and the platelet function. A represents the pressure changes in the case of the control blood, which does not contain DIDS. B represents the pressure changes in the case of the blood sample supplemented with DIDS (1.5 mg/ml), and C represents the pressure changes in the case of the perfusion with the blood supplemented with DNDS (0.3 mg/ml). It can be seen that addition of DIDS or DNDS strongly suppresses blood sedimentation, but does not affect thrombus formation, which comprehensively reflects platelets and blood coagulation.

The invention claimed is:

1. A method for testing a blood property, comprising treating blood with an erythrocyte sedimentation inhibitor, and measuring thrombogenic capacity and/or platelet function of the blood treated with the erythrocyte sedimentation inhibitor, wherein the erythrocyte sedimentation inhibitor is disodium 4,4'-dinitrostilbene-2,2'-disulfonate (DNDS), and wherein DNDS is added to blood at a final concentration of from 0.1 to 0.3 mg/ml.

2. The method according to claim 1, wherein DNDS is added to blood to a final concentration of not less than 0.2 mg/ml.

3. The method according to claim 1, wherein treating the blood with DNDS does not interfere with measurements of thrombogenic capacity and/or platelet function.

* * * * *